United States Patent [19]

Gleixner

[11] Patent Number: 4,542,011

[45] Date of Patent: Sep. 17, 1985

[54] PHARMACEUTICAL COMPOSITIONS OF XANTHINE DERIVATIVES TOLERATED BY THE STOMACH AND PROCESS FOR THEIR PREPARATION

[75] Inventor: Klaus Gleixner, Taunusstein, Fed. Rep. of Germany

[73] Assignee: Hoechst Aktiengesellschaft, Frankfurt am Main, Fed. Rep. of Germany

[21] Appl. No.: 611,104

[22] Filed: May 17, 1984

Related U.S. Application Data

[63] Continuation of Ser. No. 396,465, Jul. 8, 1982, abandoned.

[30] Foreign Application Priority Data

Jul. 10, 1981 [DE] Fed. Rep. of Germany ....... 3127237

[51] Int. Cl.[4] .................... A61K 9/24; A61K 9/28; A61K 9/32; A61K 9/36
[52] U.S. Cl. ..................................... 424/16; 424/32; 424/33; 424/35
[58] Field of Search ................ 424/16, 31–38

[56] References Cited

U.S. PATENT DOCUMENTS

| | | | |
|---|---|---|---|
| 3,864,469 | 2/1975 | Reiser et al. | 424/22 |
| 3,935,326 | 1/1976 | Groppenbacher et al. | 424/32 |
| 4,005,207 | 1/1977 | Freerksen | 424/330 |
| 4,060,598 | 11/1977 | Groppenbacher et al. | 424/32 |
| 4,064,230 | 12/1977 | Gordon et al. | 424/19 |
| 4,096,252 | 6/1978 | Barra et al. | 424/230 |
| 4,110,442 | 8/1978 | Barra et al. | 424/317 |
| 4,152,412 | 5/1979 | Harris et al. | 424/16 |
| 4,152,413 | 5/1979 | Goodnow | 424/16 |
| 4,189,469 | 2/1980 | Gleixner et al. | 424/80 |
| 4,215,113 | 7/1980 | Eriksson et al. | 424/212 |

FOREIGN PATENT DOCUMENTS

| | | |
|---|---|---|
| 0005015 | 3/1979 | European Pat. Off. . |
| 0011609 | 9/1979 | European Pat. Off. . |
| 1605467 | 5/1976 | France . |
| 2039737 | 8/1980 | United Kingdom . |

OTHER PUBLICATIONS

O. Christ et al., Arzneimittelforschung 22 (1972), p. 1933 and follow.

*Primary Examiner*—Shep K. Rose
*Attorney, Agent, or Firm*—Curtis, Morris & Safford

[57] ABSTRACT

A pharmaceutical composition of xanthine derivatives being well tolerated by the stomach and containing a mixture of granules coated with a gastric juice-resistant material and of a portion of up to 30% of granules soluble or partially soluble in gastric juice and process for its preparation.

16 Claims, No Drawings

PHARMACEUTICAL COMPOSITIONS OF XANTHINE DERIVATIVES TOLERATED BY THE STOMACH AND PROCESS FOR THEIR PREPARATION

This is a continuation of application Ser. No. 396,465 filed July 8, 1982 now abandoned.

Xanthine derivatives are in general characterized by a very disagreeable lasting bitter taste and by a bad compatibility with the stomach. The therapy of diseases, especially of children, requires pharmaceutical forms that permit an individual dosage, because of the greatly varying body weight. Generally drops or syrup are being used for said purpose. Said administration forms are excluded, however, because of the above properties of a great number of xanthine derivatives, since their bad taste cannot be masked and since the bad compatibility with the stomach is partially caused by reflexes.

Solid pharmaceutical forms have therefore been coated with films that are insoluble in gastric juice (cf. laid-open Japanese patent application No. 101417/1979; O. Christ et al., Arzneimittelforschung 22 (1972), number 11, page 1933 and follow). Said publications describe pharmaceutical forms that are coated with lacquer films insoluble in the stomach, while using organic solvents. The solvents to be evaporated represent a considerable environmental pollution problem.

The above Japanese patent application describes a process for preparing gastric juice-resistant (or enteric) pharmaceutical pellets (granules) containing the xanthine derivative pentoxyfilline. Said process has two disadvantages:

1. An organic solvent is used for the manufacture of the gastric juice-resistant coating based on hydroxypropylmethyl cellulose phthalate.

2. A great quantity of auxiliary is required for the preparation of the pellets, as a result of which 900 mg of granules contain as little as 100 mg of active ingredient (about 10–12%).

Now, it has been found that carrier pellets to which xanthine derivatives have been applied, can be coated with a gastric juice-insoluble coating, while using the gastric juice-resistant coating material in aqueous solution or dispersion. The granules obtained are distinguished by a good compatibility with the stomach.

The subject of the present invention therefore is a solid pharmaceutical composition based on granules having an improved compatibility with the stomach and containing inert carrier pellets or granules to which xanthine derivatives have been applied and which have been coated with a gastric juice-resistant coating, (a) which comprises as xanthine derivative a derivative selected from alkyl-, ($\omega$-1)-oxoalkyl- or ($\omega$-1)hydroxyalkyl-dialkylxanthine, the alkyl, oxoalkyl or hydroxyalkyl radical whereof each has from 3 to 7 carbon atoms and is in the 1- or 7-position and which derivative carries in the other 1- or 7-position an alkyl radical having from 1 to 12 carbon atoms and in the 3-position an alkyl radical having from 1 to 4 carbon atoms, (b) wherein the gastric juice-resistant coating has been applied in the form of an aqueous solution or aqueous dispersion and (c) wherein only part of the granules have been coated with a gastric juice-resistant coating, the pharmaceutical composition containing from 20 to 50% of xanthine derivative, from 30 to 80% of inert carrier material and from 5 to 40% of gastric juice-insoluble coating material and the portion of granules soluble or partially soluble in gastric juice amounting up to 30%.

Suitable xanthine derivatives are in particular the following compounds:

Oxohexyldimethylxanthines wherein the oxohexyl radical is either in the 1- or in the 7-position, 1-(4-hydrooxypentyl)- and 1-(5-hydroxyhexyl)-3,7-dimethylxanthine, 7-(4-hydroxypentyl)- and 7-(5-hydroxyhexyl)-1,3-dimethylxanthine, 1-(4-oxopentyl)-, 1-(2-methyl-3-oxobutyl)- and 1-(2-ethyl-3-oxobutyl)-3,7-dimethylxanthine as well as 7-(4-oxopentyl)-, 7-(2-methyl-3-oxobutyl)- and 7-(2-ethyl-3-oxobutyl)-1,3-dimethylxanthine.

Further suitable xanthines are hydroxyalkyl- or oxoalkylxanthines which contain in the 1- or 7-position an alkyl group having up to 4 carbon atoms instead of a methyl group, for example 1-ethyl-, 1-propyl-, 1-butyl- and 1-isobutyl-3-methyl-7-(5-hydroxyhexyl)-xanthine and the corresponding compounds wherein said alkyl radicals are in the 7-position and the hydroxyalkyl or oxoalkyl radical, respectively, is in the 1-position. Particularly preferred are 1-(5-oxohexyl)-3,7-dimethylxanthine and 3-methyl-1-(5-oxohexyl)-7-propylxanthine.

The inert carrier pellets or granules consist, for example, of sugar, lactose, microcrystalline cellulose or a plastics material.

The gastric juice-insoluble coating is dissolved preferably at a pH above 5.5. The following coatings, aqueous solutions or dispersions, respectively, which are suitable for the preparation of gastric juice-resistant coatings, may be used according to the invention:

1. Substances based on polyacrylic resin lacquers such as copolymers based on poly(meth)acrylic acid and poly(meth)acrylic acid esters (Eudragit ®L30 D).

2. Hydroxypropylcellulose phthalate, a fine powder (20-30 $\mu$m) for example HP 55 F of Shin-Etsu Chemicals Co., Tokyo) in conjunction with a softener (for example triacetin).

3. An aqueous suspension of a copolymer of 90 weight parts of vinyl acetate and 10 weight parts of crotonic acid (for example Coating CE 5142 furnished by BASF, Germany).

The preparation of granules and their subsequent coating with film-forming substances is difficult, since they partially adhere to each other to form agglomerates of considerable dimension, which results in a high reject rate. It has now been found surprisingly that a good compatibility with the stomach is guaranteed even if the pharmaceutical form contains in addition to gastric juice-insoluble granules a portion of up to 30% of granules that are soluble or partially soluble in gastric juice.

Subject of the present invention therefore also is a process for the preparation of said pharmaceutical composition based on granules having an improved compatibility with the stomach, which comprises coating the carrier pellets or granules coated with the xanthine derivative by means of an aqueous solution or dispersion of a gastric juice-resistant coating material, separating the agglomerates obtained by sieving on an appropriate sieve, crushing them in a granulator and admixing the granules obtained, which are soluble or partially soluble in gastric juice to the granules coated with the gastric juice-resistant material, the portion of granules soluble or partially soluble in gastric juice amounting up to 30%.

Losses due to the process applied are avoided nearly completely in the process according to the invention. On principle, it is possible to mix gastric juice-resistant granules with a portion of granules soluble or partially soluble in gastric juice amounting up to 30%, the latter having not been obtained in the course of the process of the invention.

The process according to the invention makes it possible to process or to administer the same quantity of active ingredient as in the processes hereto known while using a far smaller quantity of auxiliary. The aqueous solution or dispersion of the film-forming material may contain the usual additives.

The present invention permits the administation or processing of the same quantity of active ingredient as in the previously known processes while using less than half of the quantity of auxiliary.

The preparation or the process of the invention has, consequently, the following advantages:

1. Economic advantages: savings of auxiliary, practically no losses in material, no organic solvents.
2. The preparation of the granules requires no complicated machinery (only a coating vessel, a vibrating sieve, a granulator and a mixer).
3. The process limits polluting, since the preparation of the granules requires only aqueous solutions or dispersions.
4. Possibility of individual dosage using a small quantity of granules, which is particularly important in pediatric practice, more particularly with children suffering, for example, from peripheric circulatory disturbances caused by diabetes, inflammation or functional disorders.

The dosage depends on the body weight. A treatment of adults requires the administration of up to three doses of from 100 to 200 mg of active ingredient a day, whereas doses of from 25 to 100 mg, depending on the body weight, are sufficient with children. Granules are frequently dosed in rigid gelatin capsules. When bringing the granules according to the invention into dosage units (compressed volume 0.85 g/ml), the standard dose of 100 mg of active ingredient may be put into a capsule of size 1, whereas a capsule of at least size 00 is required in the case of granules according to Japanese OLS No. 101417/1979, that means the charge volume is probably to small. Taking a capsule of size 00 can practically not be expected of humans, in particular of children. Even if the dose would be divided up to two capsules, a capsule of size 0 would still be required.

Dividing the standard dose up to several capsules moreover involves the danger of underdosage, as patients may take one capsule only.

The following quantities of active ingedient may be filled into capsules according to the process of the invention:

| dose mg/capsule active ingredient | size of the capsule |
|---|---|
| 200 | 00 |
| 100 | 1 |
| 75 | 2 |
| 50 | 3 |
| 25 | 4 |

Alternatively, the granules may be filled into single dosage bags or they may be compressed into tablets upon admixture with further auxiliaries. The granules according to the invention, consequently, permit an individual treatment while using appropiate pharmaceutical forms, which are prepared by little polluting, material- and cost-saving processes.

The active ingredient is released in delayed manner from the pharmaceutical form according to the invention. Depending on the portion of soluble or partially soluble granules, up to 30% of active ingredient is released in the stomach, whereas the residual part is released in delayed manner in the intestinal zone.

The following examples illustrate the invention:

EXAMPLES 1. 100 g of sugar pellets are humidified in an operating coating vessel with a 70% sugar syrup containing additionally gum arabic and talc. Onto the humid pellets there is strewed portionwise a powder mixture consisting of 100 g of 1-(5-oxohexyl)-3,7-dimethylxanthine,
25 g of talc and
10 g of silicon dioxide.

The coated sugar pellets have a final weight of about 350 g. Upon drying, the granules are sprayed in the coating vessel with a sufficient quantity of a 15% aqueous polyacrylic resin dispersion (Eudragit L30 D) containing additionally 1.5% of polyethylene glycol, 1% of polyvinyl pyrrolidone, 3% talc and 1% of titanium dioxide (dry substance about 50 g). The total weight amounts to about 400 g.

Subsequently, the agglomerates are separated by sieving on a sieve having a mesh diameter of 1.5 mm and crushed on a sieve having a mesh diameter of 1.6 mm. A portion up to 30% of the crushed agglomerates obtained is added to the resistant granules.

2. 100 g of 1-(hexyl)-3,7-dimethylxanthine are processed to granules in the manner described in step 1.

3. 100 g of 1-(5-hydroxyhexyl)-3,7-dimethylxanthine are applied to mannitol pellets in the manner described in Example 1 and processed to granules.

4. 100 g of 1-propyl-3-methyl-7-(5-hydroxyhexyl)xanthine are applied to lactose-based granules prepared on a pelletizing disk in the manner described in Example 1 and the coated granules are provided with a second coating consisting of a 10% aqueous film-coating suspension based on vinyl acetate/crotonic acid and are processed in the manner described in Example 1.

What is claimed is:

1. A pharmaceutical composition based on granules having an improved compatibility with the stomach and containing inert carrier pellets or granules to which xanthine derivatives have been applied and which have been coated with a gastric juice-resistant coating,
   (a) which comprises as xanthine derivative a derivative selected from alkyl-, ($\omega$-1)-oxoalkyl- or ($\omega$-1)-hydroxyalkyldialkylxanthine, the alkyl, oxoalkyl or hydroxyalkyl radical whereof each has from 3 to 7 carbon atoms and is in the 1- or 7-position and which derivative carries in the other 1- or 7-position an alkyl radical having from 1 to 12 carbon atoms and in the 3-position an alkyl radical having from 1 to 4 carbon atoms,
   (b) wherein the gastric juice-resistant coating has been applied in the form of an aqueous solution or aqueous dispersion,
   (c) wherein only part of the granules have been coated with a gastric juice-resistant coating, the pharmaceutical composition containing from 20 to 50% of xanthine derivative, from 30 to 75% of inert carrier material and from 5 to 40% of gastric juice-insoluble coating material and the portion of granules soluble or partially soluble in gastric juice amounting up to 30% and (d) wherein the gastric juice-resistant coating is a polyacrylic resin, a hydroxypropylcellulose phthalate or an aqueous suspension of a copolymer of 90 parts by weight of a vinyl acetate and 10 parts by weight of a crotonic acid.

2. The pharmaceutical composition according to claim 1, which comprises up to 300 mg of active ingredient contained in a capsule, a tablet or a small envelope.

3. The pharmaceutical composition, according to claim 1, wherein the gastric juice-resistant coating is a polyacrylic resin.

4. The pharmaceutical composition, according to claim 1, wherein the gastric juice-resistant coating is a copolymer of a poly(meth)acrylic acid or a poly(meth)acrylic acid ester.

5. The pharmaceutical composition, according to claim 1, wherein the gastric juice-resistant coating is a hydroxypropylcellulose phthalate.

6. The pharmaceutical composition according to claim 1, wherein the gastric juice-resistant coating is an aqueous suspension of a copolymer of 90 parts by weight of a vinyl acetate and 10 parts by weight of a crotonic acid.

7. A process for preparing the pharmaceutical composition according to claim 1, which comprises coating the carrier pellets or granules to which the xanthine derivatives have been applied, with an aqueous solution or aqueous dispersion of a gastric juice-resistant coating material, separating the agglomerates obtained by sieving on an appropriate sieve, crushing said agglomerates in a granulator and admixing the granules thus obtained, which are soluble or partially soluble in gastric juice, to the granules provided with a gastric juice-resistant coating, the portion of granules soluble or partially soluble in gastric juice amounting up to 30%.

8. A process as claimed in claim 7 wherein the final mixture is filled in a capsule or a small envelope or is compressed with further auxiliaries into tablets.

9. The pharmaceutical composition according to claim 1, wherein the alkyl, oxoalkyl or hydroxyalkyl radical of the xanthine derivative is in the 1-position.

10. The pharmaceutical composition according to claim 1, wherein the alkyl-, oxoalkyl- or hydroxyalkyl-radical of the xanthine derivative has 6 carbon atoms.

11. The pharmaceutical composition according to claim 9, wherein the alkyl, oxoalkyl or hydroxyalkyl radical of the xanthine derivative has 6 carbon atoms and wherein the xanthine derivative has in the 3-position a methyl radical.

12. The pharmaceutical composition according to claim 11, wherein the xanthine derivative is 1-(5-oxohexyl)-3,7-dimethyl-xanthine.

13. The pharmaceutical composition according to claim 1, wherein the xanthine derivative is 1-hexyl-3,7-dimethyl-xanthine.

14. The pharmaceutical composition according to claim 1, wherein the granules are in a free-flowing state.

15. A pharmaceutical composition comprising inert carrier pellets or granules to which a xanthine derivative has been applied and which have been coated with a gastric juice-resistant coating means for improving the compatibility of the xanthine derivative with the stomach, wherein a. the xanthine derivative is a derivative selected from alkyl-, ($\omega$-1)-oxoalkyl- or ($\omega$-1)-hydroxyalkyl-dialkylxanthine, the alkyl, oxoalkyl or hydroxyalkyl radical of which each has from 3 to 7 carbon atoms and is in the 1- or 7-position and which derivative carries in the other 1- or 7-position an alkyl radical having from 1 to 12 carbon atoms and in the 3-position an alkyl radical having from 1 to 4 carbon atoms, b. the gastric juice-resistant coating means is applied in the form of an aqueous solution or aqueous dispersion, c. a portion of the pellets or granules have been coated with the gastric juice-resistant coating means, the pharmaceutical composition containing from 20 to 50% of xanthine derivative, from 30 to 75% of inert carrier material and from 5 to 40% of gastric juice-insoluble coating means and the portion of granules soluble or partially soluble in gastric juice amounting up to 30% and d. the gastric juice-resistant coating means comprises a polyacrylic resin, a hydroxypropylcellulose phthalate or an aqueous suspension of a copolymer of 90 parts by weight of a vinyl acetate and 10 parts by weight of a crotonic acid.

16. The pharmaceutical composition according to claim 1, wherein the xanthine derivative is 1-(5-oxohexyl)-3-methyl-7-propylxanthine.

* * * * *